United States Patent [19]

Mencke et al.

[11] Patent Number: 6,159,932
[45] Date of Patent: Dec. 12, 2000

[54] ENDOPARASITICIDAL COMPOSITIONS

[75] Inventors: Norbert Mencke, Leverkusen; Achim Harder, Köln; Peter Jeschke, Leverkusen; Barbara Kölbl, Köln, all of Germany

[73] Assignee: Bayer Aktiengesellschaft, Leverkusen, Germany

[21] Appl. No.: 08/952,356

[22] PCT Filed: May 20, 1996

[86] PCT No.: PCT/EP96/02170

§ 371 Date: Nov. 19, 1997

§ 102(e) Date: Nov. 19, 1997

[87] PCT Pub. No.: WO96/38165

PCT Pub. Date: Dec. 5, 1996

[30] Foreign Application Priority Data

Jun. 2, 1995 [DE] Germany .................. 195 20 275

[51] Int. Cl.[7] .................. A61K 38/00; A61K 31/70; A61K 31/335

[52] U.S. Cl. ................ 514/9; 514/11; 514/30; 514/450

[58] Field of Search .................. 514/9, 11, 30, 514/450

[56] References Cited

U.S. PATENT DOCUMENTS

| | | | |
|---|---|---|---|
| 4,310,519 | 1/1982 | Albers-Schonberg et al. | 424/181 |
| 4,468,390 | 8/1984 | Kitano | 424/232 |
| 5,589,503 | 12/1996 | Mencke et al. | 514/450 |
| 5,663,140 | 9/1997 | Scherkenbeck et al. | 514/11 |
| 5,821,222 | 10/1998 | Bonse et al. | 514/11 |

FOREIGN PATENT DOCUMENTS

| | | |
|---|---|---|
| 0382173 | 8/1990 | European Pat. Off. |
| 95/05181 | 2/1995 | WIPO |

*Primary Examiner*—Kevin E. Weddington
*Attorney, Agent, or Firm*—Joseph C. Gil; Godfried R. Akorli

[57] ABSTRACT

The present invention relates to mixtures of avermectins, 22,23-dihydroavermectins $B_1$ (ivermectins) and milbemycins from the class of the macrocyclic lactones in combination with cyclic depsipeptides, optionally in the presence of praziquantel or epsiprantel, for increasing the endoparasiticidal action in endoparasiticidal compositions.

20 Claims, No Drawings

ENDOPARASITICIDAL COMPOSITIONS

The present invention relates to mixtures of avermectins, 22,23-dihydroavermectins $B_1$ (ivermectins) and milbemycins from the class of the macrocyclic lactones in combination with cyclic depsipeptides, optionally in the presence of praziquantel or epsiprantel, for increasing the endoparasiticidal action in endoparasiticidal compositions.

Gastrointestinal nematode infections of dogs are in most cases brought about by species of the three nemadode families Ascarididae, Ancylostomatidae and Trichuridae. In cats, it is predominantly the two nemadode families Ascarididae and Ancylostomatidae which have spread worldwide. After passing through a number of development stages in a very great diversity of tissues of the host animals, patent infection of the gastrointestinal tract occurs. During the prepatency and patency of the infection, the parasitosis of roundworms, hookworms and whipworms causes considerable problems, especially in young, growing dogs, cats and also in humans. Therapy or prophylactic treatment is therefore an urgent necessity in order both to cure animals already affected and to maintain as yet uninfected animals in a healthy condition.

Consequently, the protection of dogs and cats against infection is of very great importance as prophylaxis against human infections, especially in children.

A series of nematicidal substances are already used as anthelminthics in animal breeding. In order to achieve effective protection, increasing use is being made not only of the pure compound but also of combinations of two or more substances.

Nevertheless, the effectiveness of these known combinations against parasites, especially at low dosages, is not always entirely satisfactory.

In addition to the gastrointestinal helminthic diseases in dogs and cats, as already mentioned, there are further severe parasitoses, for example filiarioses, which are highly host-specific.

The parasite *Dirofilaria immitis*—a filaria endemic in parts of North to South America, Africa, Asia and also Australia, is the cause of the important canine and feline cardiovascular dirofilariosis. The severe pathophysiological changes within the cardiovascular system which occur during the *Dirofilaria immitis* infection of dogs and cats can bring about a dramatic course of the disease in the host animal.

Among the known compounds with anthelmintic activity, only a few possess efficiency as a prophylactic against *Dirofilaria immitis*.

Anthelminthics such as, for example, diethylcarbamazine (DEC), although effective, must be administered daily during transmission (mosquito) of the pathogen. With the introduction of the anthelminthics ivermectin/milbemycin from the class of the macrocyclic lactones, it has been possible to reduce the prophylactic treatment of dogs and cats to one monthly administration.

Although there are endoparasiticidal agents having a high level of efficiency against gastrointestinal nematodes and other agents with an action against *Dirofilaria immitis* in dogs and cats, none of the known compounds has as yet shown the kind of broad-spectrum action which would make it suitable for use as a therapeutic agent against all gastrointestinal nematodes and as a prophylactic agent against *Dirofilaria immitis*.

For this reason, a variety of active substance combinations are employed which exhibit an improved action and have, moreover, reduced side-effects and toxicity in the host.

In the majority of cases, the monthly prophylaxis of *Dirofilaria immitis* is carried out with an avermectin, for example ivermectin, from the class of the macrocyclic lactones in combination with an anthelminthic, such as pyrantel or a benzimidazole, e.g. albendazole (cf W. C. Campbell, Ann. Rev. Microbiol. 45 (1991), pp. 445–474; J. N. Clark et al. Am. J. Vet. Res. 53(4), (1992), pp. 517–520).

A combination which may be mentioned by way of example is one consisting of 6.0 µg/kg ivermectin and 5.0 mg/kg pyrantel pamoate. While this combination ensures treatment and control of Ascarides (*T. canis* and *T. leonina*) and of hookworms (*A. canis* and *U. steneocephala*), it cannot be employed against whipworms (*T. vulpis*). Milbemycin as well, at 500 µg/kg, shows a distinct weakness in its action against the hookworm *Uncinaria stenocephala* a gastrointestinal nematode which causes severe parasitaemia in young dogs (cf. D. D. Bowman et al. Am. J. Vet. Res. 51 (1990) p. 487; R. Grieve J. Am. Vet. Assoc. 194 (1989), p. 1815).

In addition to this, ivermectin has been tested successfully in human medicine as an agent against filaria infections and against various gastrointestinal nematode infections. However, these studies too have shown that ivermectin, despite a high dosage on several days in succession, is ineffective in hookworm and whipworm infected patients (cf Otteson & Campbell, J. Antimicrob. Chemother. 34, 1994, pp. 195–203).

These reasons make it clear that avermectins, 22,23-dihydroavermectins $B_1$ (ivermectins) and milbemycins from the class of the macrocyclic lactones, both on their own and in combination with an anthelmintic, have not to date been able to act at the same time at low dosages against roundworms, hookworms and whipworms in the gastrointestinal tract of dogs and cats.

The present invention relates to endoparasiticidal compositions which comprise at least one avermectin, 22,23-dihydroavermectin $B_1$ (ivermectins) or milbemycin from the class of the macrocyclic lactones in combination with cyclic depsipeptides consisting of amino acids and hydroxycarboxylic acids as ring structural units and 6 to 30 ring atoms, optionally in the presence of praziquantel or epsiprantel.

The compositions according to the invention, of a combination of at least one avermectin, 22,23 dihydroavermectin $B_1$ (ivermectin) or milbemycin from the class of the macrocyclic lactones with cyclic depsipeptides consisting of amino acids and hydroxycarboxylic acids as ring structural units and 6 to 30 ring atoms, exhibit an unexpected synergistic effect.

This synergistic effect in the endoparasiticidal composition according to the invention, brought about with a combination of at least one avermectin, 22,23-dihydroavermectin $B_1$ (ivermectin) or milbemycin from the class of the macrocyclic lactones with cyclic depsipeptides consisting of amino acids and hydroxycarboxylic acids as ring structural units and 6 to 30 ring atoms, is retained even in the presence of praziquantel or epsiprantel.

Avermectins have been isolated as microbial metabolites from the microorganism Streptomyces avermitilis (U.S. Pat. No. 4,310,519) and can occur predominately as a mixture consisting of the eight components $A_{1a}$, $A_{1b}$, $A_{2a}$, $A_{2b}$, $B_{1a}$, $B_{1b}$, $B_{2a}$ and $B_{2b}$ (I. Putter et al. Experentia 37 (1981) p. 963, Birkhäuser Verlag (Switzerland).

There is also interest in the synthetic derivatives, especially 22,23 dihydroavermectin $B_1$ (ivermectin) (U.S. Pat. No. 4,199,569). Similarly, milbemycin B-41 D has been isolated by fermentation from Streptomyces hygroscopicus (cf. "Milbemycin: Discovery and Development" I. Junya et al. Annu. Rep. Sankyo Res. Lab. 45 (1993), pp. 1–98; JP Pat. 8 378 549; GB 1 390 336).

The use of avermectins, 22,23 dihydroavermectins $B_1$ (ivermectins) and milbemycins from the class of the macrocyclic lactones as endoparasiticides has been known for a long time and is the subject of numerous patent applications and review articles (e.g. Biological effects in: "Ivermectin and Abamectin" W. C. Campbell, Ed., Springer Verlag, New York, N.Y., 1989; "Avermectins and Milbemycins Part II" H. G. Davies et al. Chem. Soc. Rev. 20 (1991) pp. 271–339; Chemical modifications in: G. Lukacs et al. (Eds.), Springer-Verlag, N.Y., (1990), Chapter 3; Cydectin™ [moxidectin and derivatives]: G. T. Carter et al. J. Chem. Soc. Chem. Com-mun. (1987), pp. 402–404); EP 423 445-A1). The use of Doramectin (Pfizer) as an endoparasiticide is also known (cf. "Doramectin—a potent novel endectozide" A. C. Goudie et al. Vet. Parasitol. 49 (1993), pp. 5–15).

Furthermore, combinations of averrnectins, 22,23-dihydroavermectins $B_1$ (ivermectins) or milbemycins with particular classes of anthelminthics, for example benzimidazoles, salicylamides, levamisole, pyrantel or praziquantel, are the subject of numerous patent applications (e.g.: GB 2 252 730; GB 2 224 933; GB 2 21 3 722; EP-A 59 074).

A cyclic depsipeptide PF 1022 A and its action against endoparasites is known from EP-A 382 173 and EP-A 503 538 (total synthesis of PF 1022 A: JP Patent 05 229 997; Makoto Ohyama et al., Biosci. Biotech. Biochem. 58 (6), 1994, pp. 1193–1194; Makio Kobayshi et al., Annu. Rep. Sankyo Res. Lab. 46, 1994, pp. 67–75; stephen J. Nelson et al., J. Antibiotics 47, (11), 1994, pp. 1322–1327).

Further cyclic depsipeptides and their endoparasiticidal action are the subject of published or non-prior published (cyclooctadepsipeptides: WO 93/19053; EP 0 634 408 A1; WO 94/19334; WO 95/07272; EP 626 375; EP 626 376; cyclo-hexadepsipeptides: DE-A 4342 907; WO 93/25543; DE-A 4 437 198.5; DE-A 4 440 193.0 and cyclotetradepsipeptides: EP-OS 664 297) patent applications.

Praziquantel 2-(cyclohexylcarbonyl)-1,2,3,6,7,11 b-hexahydro-4H-pyrazino[2,1-a]-isoquinolin-4-one and its action against endoparasites is known from DE-P 2 362 539, U.S. Pat. No. 4,001,411.

Epsiprantel 2-(cyclohexylcarbonyl)-2,3,6,7,8,12b-hexahydro-pyrazino[2,1-a][2]-benzazepin-4(1H)-one and its action against endoparasites is known from EP-A 13 4 984, EP-A 185 012.

The use of praziquantel and epsiprantel for increasing the endoparasiticidal action of cyclic depsipeptides consisting of amino acids and hydroxycarboxylic acids as ring structural units and 6 to 30 ring atoms is known from EP-A 662 326.

The present invention therefore relates to endoparasiticidal compositions which comprise at least one avermectin, 22,23-dihydroavermectin $B_1$ (ivermectin) or milbemycin from the class of the macrocyclic lactones in combination with cyclic depsipeptides consisting of amino acids and hydroxycarboxylic acid as ring structural units and 6 to 30 ring atoms, optionally in the presence of praziquantel or epsiprantel.

The present invention additionally relates to the use of avermectins, 22,23di-hydroavermectins $B_1$ (ivermectins) and milbemycins from the class of the macrocyclic lactones in combination with cyclic depsipeptides consisting of amino acids and hydroxycarboxylic acids as ring structural units and 6 to 30 ring atoms, optionally in the presence of praziquantel or epsiprantel, for the preparation of endparasiticidal compositions.

Examples which may be mentioned of co-components from the group of the microbial metabolites are the avermectins and derivatives thereof. These compounds constitute a mixture of macrolide lactones of the general formula (I)

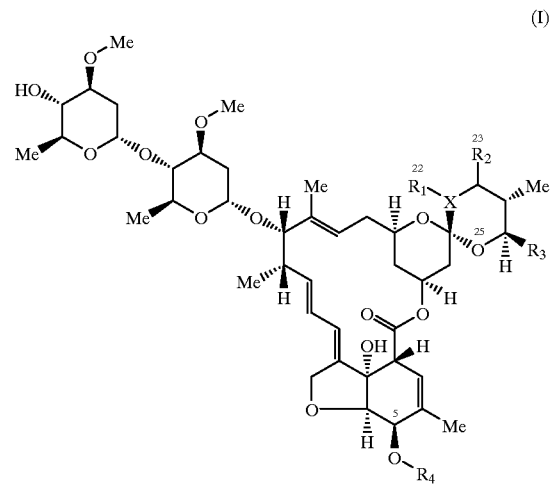

in which
the radicals $R^1$ to $R^4$ can have the meaning given in Table 1 below and X can represent a single or double bond between the $C_{22}$ and $C_{23}$ po-sition ($—C_{22}R^1—X—C_{23}R^2—$).

In the case of a double bond there are no substituents ($R^1$, $R^2$) at the $C_{22}$ and $C_{23}$ position.

TABLE 1

| Macrocyclic lactone | $-C_{22}R^1-X-C_{23}R^2-$ | $R^3$ | $R^4$ |
|---|---|---|---|
| Avermectin $A_{1a}$ | —CH=CH— | -sec-Bu | —Me |
| Avermectin $A_{1b}$ | —CH=CH— | -iso-Pr | —Me |
| Avermectin $A_{2a}$ | —CH$_2$—CHOH— | -sec-Bu | —Me |
| Avermectin $A_{2b}$ | —CH$_2$—CHOH— | -iso-Pr | —Me |
| Avermectin $B_{1a}$ | —CH=CH— | -sec-Bu | —H |
| Avermectin $B_{1b}$ | —CH=CH— | -iso-Pr | —H |
| Avermectin $B_{2a}$ | —CH$_2$—CHOH— | -sec-Bu | —H |
| Avermectin $B_{2b}$ | —CH$_2$—CHOH— | -iso-Pr | —H |
| 22,23-dihydroavermectin $B_{1a}$ | —CH$_2$—CH$_2$— | -sec-Bu | —H |
| 22,23-dihydroavermectin $B_{1b}$ | —CH$_2$—CH$_2$— | -iso-Pr | —H |
| Doramectin | —CH=CH— | -Chx | —H |

22,23-dihydroavermectin $B_1$ represents ivermectin $B_1$; sec-Bu=secondary butyl; iso—Pr=isopropyl; Chx=cyclohexyl; —Me=methyl The avermectins and 22,23-dihydroavermectins $B_1$ (ivermectins) of the general formula (I) are in general employed as mixtures. In this context, particular interest attaches to the product abamectin, which essentially comprises the avermectins $B_1$, and hydrogenation products thereof, the 22,23-dihydroavermectins $B_1$ (ivermectin).

The compounds labelled "b" of the macrocyclic lactones, which possess an isopropyl radical in the $C_{25}$ position, need not necessarily be separated from the "a" compounds, which have a sec-butyl group in the $C_{25}$ position. Generally the mixture of both substances is isolated, consisting of >80% sec-butyl derivative ($B_{1a}$) and <20% iso-propyl derivative ($B_{1b}$), and can be used in accordance with the invention. Moreover, in the case of the stereoisomers, the substituents in the $C_{13}$ and $C_{23}$ position can be arranged in both α and β configuration on the ring system, i.e. can be located above or below the plane of the molecule. In each case, all of the stereoisomers are taken into account in accordance with the invention.

The milbemycins have the same macrolide ring structure as avermectins or 22,23-dihydroavermectins $B_1$ (ivermectins), but carry no substituent (i.e. missing oleandrose disaccharide fragment) in position 13 ($R^5$=hydrogen).

As milbemycins from the class of the macrocyclic lactones, mention may be made by way of example of the compounds having the general formula (II)

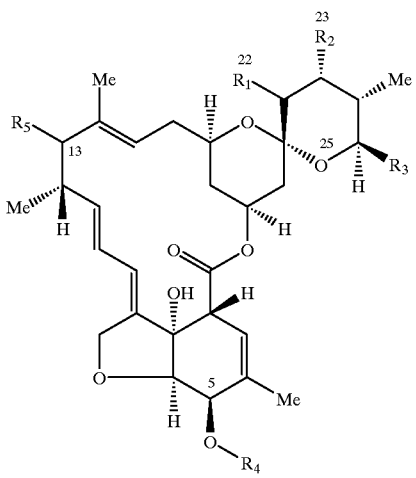

(II)

in which the radicals $R^1$ to $R^5$ have the meaning given in Table 2 below:

TABLE 2

| Macrocyclic lactone | $R^1$ | $R^2$ | $R^3$ | $R^4$ | $R^5$ |
|---|---|---|---|---|---|
| Milbemycin B41 D | —H | —H | -iso-Pr | —H | —H |
| Nemadectin | —H | —OH | (Me)₂C=CH-CH(Me)- | —H | —H |
| Moxidectin | —H | =N—O—Me | (Me)₂C=CH-CH(Me)- | —H | —H | iso-Pr = isopropyl

Among the co-components for the compounds of the formula (I) and (II), the following macrocyclic lactones are of particular interest in accordance with the invention:

Avermectin $B_{1a}/B_{1b}$ 22,23-Dihydroavermectin $B_{1a}/B_{1b}$ (or ivermectin $B_{1a}/B_{1b}$)

Doramectin

Moxidectin

Preferred co-components with above macrocyclic lactones of the formula (I) and (II) are, in accordance with the invention, cyclic depsipeptides having 24 ring atoms.

The depsipeptides with 24 ring atoms include compounds of the general formula (III)

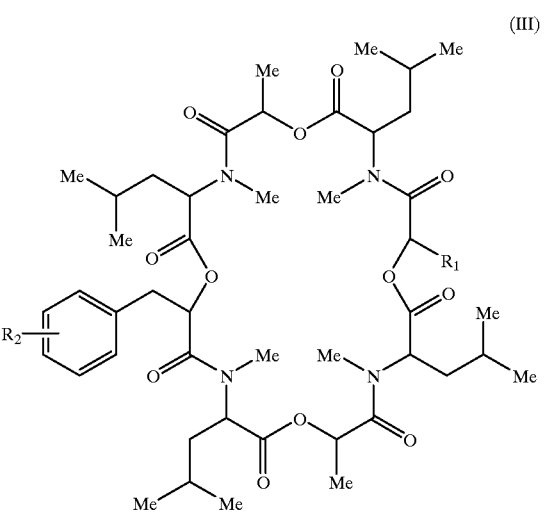

(III)

in which $R^1$ represents optionally substituted benzyl, substituents which may be mentioned being hydrogen, $C_{1-4}$-alkyl, especially methyl, hydroxyl, halogen, especially fluorine, $C_{1-4}$-alkoxy, especially methoxy or tert-butyloxy, nitro, amino, dialkylamino, especially dimethylamino or diethylamino, N-morpholinyl, N-pyrrolidinyl or N-piperidinyl, $R^2$ represents hydrogen, $C_{1-4}$-alkyl, especially methyl, hydroxyl, halogen, especially fluorine, $C_{1-4}$-alkoxy, especially methoxy or tert-butyloxy, nitro, amino, dialkylamino, especially dimethylamino or diethylamino, N-mor-pholinyl, N-pyrrolidinyl or N-piperidinyl, where a) when $R^1$ represents benzyl
$R^2$ represents hydrogen, hydroxyl, $C_{1-4}$-alkoxy, especially methoxy, halogen, especially fluorine, alkenyloxy, especially allyloxy, b) when $R^1$ represents methyl
$R^2$ represents hydrogen, hydroxyl, $C_{1-6}$-alkoxy, especially methoxy, nitro, amino, dialkylamino, especially dimethylamino, N-morpholinyl.

In the context of the present invention, it is possible to use all compounds of the general formula (III), which can exist in optically active, stereoisomeric forms or as racemic mixtures. It is preferred in accordance with the invention, however, to use the optically active, stereoisomeric forms of the compounds of the general formula (III). Particular preference is given to the use of the cyclic depsipeptides composed of L-configured amino acids and D-configured hydroxycarboxylic acids as ring structural units.

One example of a cyclic depsipeptide which may be mentioned is the compound PF 1022A, known from EP-A 382 173 and EP-A 503 538, of the following formula (IIIa), in which $R^1$ represents benzyl and $R^2$ represents hydrogen:

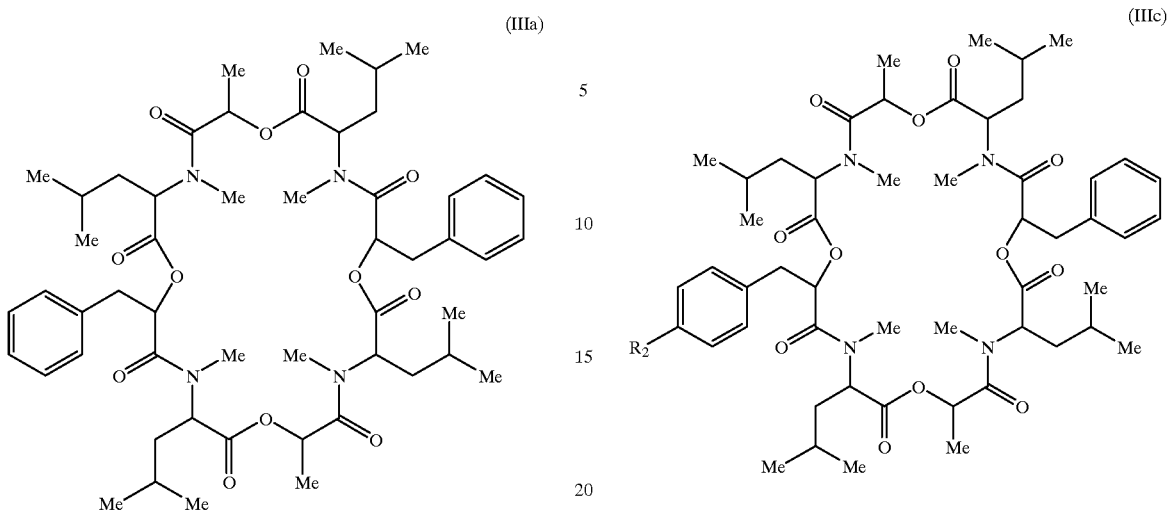

(IIIa)

Other depsipeptides which may be mentioned are the compounds known from PCT Application WO 93/19053 and EP 0 634 408 A1.

Particular mention may be made of the compounds from the PCT Application WO 93/19053 and EP 0 634 408 A1 which are of the following formula (IIIb), in which $R^1$ represents ($R^3$) substituted benzyl:

(IIIb)

in which $R^2$ and $R^3$ represent N-morpholinyl, nitro, amino, mono- or dimethylamino.

Additional depsipeptides which may be mentioned are the compounds known from PCT Application WO 94/19334.

Particular mention may be made of the compounds from PCT Application WO 94/19334 which are of the following formula (IIIc), in which $R^1$ represents benzyl:

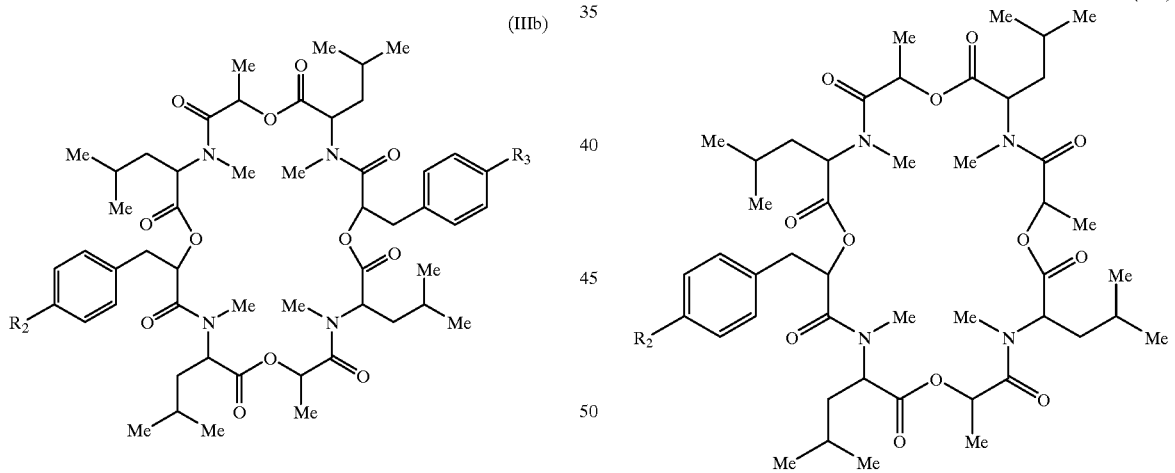

(IIIc)

in which $R^2$ represents hydroxyl, methoxy or tert-butoxy.

Finally, depsipeptides which may be mentioned are the compounds known from PCT Application WO 95/07272.

Particular mention may be made of the compounds from PCT Application WO 95/07272 which are of the following formula (IIId), in which $R^1$ represents methyl:

(IIId)

in which $R^2$ represents methoxy, dimethylamino or N-morpholinyl.

According to the most preferred composition of the endoparasiticidal compositions according to the invention, the 22, 23-dihydroavermectins $B_{1a}/B_{1b}$ (ivermectins $B_{1a}/B_{1b}$) of the general formula (Ia) from the class of the macrocyclic lactones (Ia)

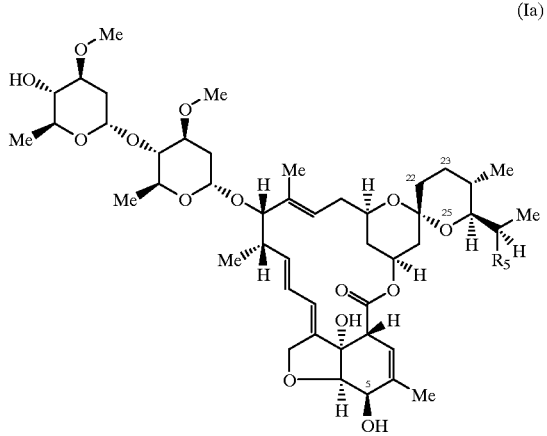

in which
R[5] represents methyl and ethyl
together with the cyclic depsipeptide PF 1022A of the formula (IIIa)

(IIIa)

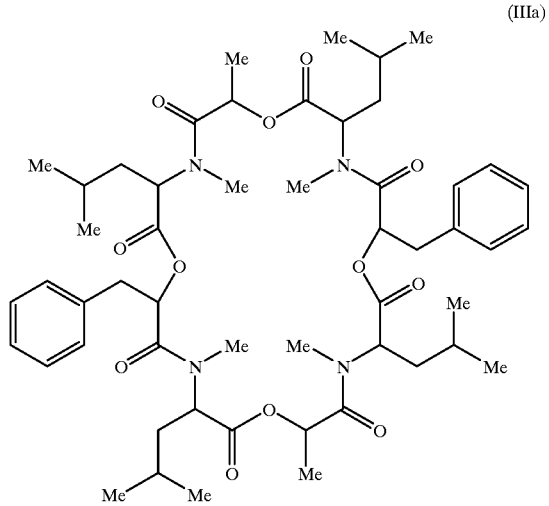

are combined with one another, optionally in the presence of praziquantel or epsiprantel, as co-components in the present invention, in a synergistically effective ratio.

According to a further specific preferred composition of the endoparasiticidal compositions according to the invention, the 22,23-dihydroavermectins $B_{1a}/B_{1b}$ (ivermectins $B_{1a}B_{1b}$) of the general formula (Ia) from the class of the macrocyclic lactones (Ia)

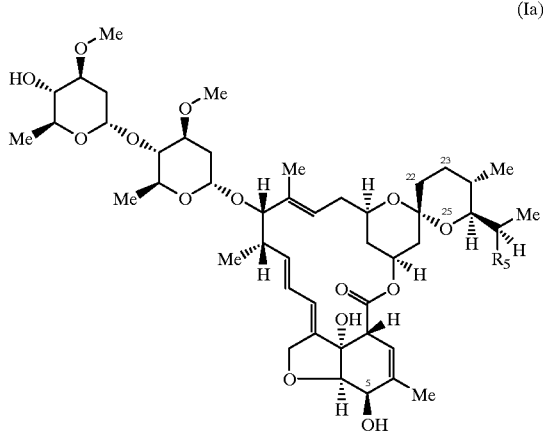

in which

R[5] represents methyl and ethyl
together with the cyclic depsipeptide of the formula (IIIb)

(IIIb)

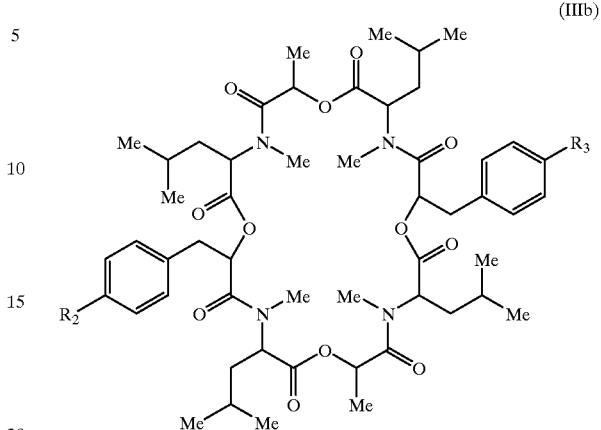

in which
R[2] and R[3] represents N-morpholinyl
are combined with one another, optionally in the presence of praziquantel or epsiprantel, as co-components in the present invention, in a synergistically effective ratio.

In accordance with the invention, the compounds of the formula (I) or (II) and (III) can also be combined with two or more of the active substances listed, optionally in the presence of praziquantel or epsiprantel.

The endoparasiticidal activity of the active substance combinations according to the invention is markedly higher than was to be expected from the actions of the individual components. Therefore, by employing these combinations, it is possible to reduce the application rate of the individual components. Their use, accordingly, brings with it economic and ecological advantages.

While having low toxicity to warm-blooded species, the compositions according to the invention are suitable for combating pathogenic endoparasites which occur in humans and in animal keeping and animal breeding in useful animals, breeding animals, zoo animals, laboratory animals, animals for experimentation and hobby animals. In this context they are active against all or individual stages of development of the pests and against resistant and normally sensitive species. By combating the pathogenic endoparasites the intention is to reduce disease, mortality and reductions in yield (for example in the production of meat, milk, wool, hides, eggs, honey, etc.), so that the use of the active substances enables more economic and simpler animal keeping. The pathogenic endoparasites include cestodes, trematodes, nematodes and Acantocephala, in particular:

From the order of the Pseudophyllidea, for example: Diphyllobothrium spp., Spirometra spp., Schistocephalus spp., Ligula spp., Bothridium spp., Diplogonoporus spp.

From the order of the Cyclophyllidea, for example: Mesocestoides spp., Anoplocephala spp., Paranoplocephala spp., Moniezia spp., Thysanosomsa Spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.

From the subclass of the Monogenea, for example: Gyrodactylus spp., Dactylogyrus spp., Polystoma spp.

From the subclass of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp-, Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp. Metorchis spp., Heterophyes spp., Metagonimus spp.

From the order of the Enoplida, for example: Trichuris spp., Capillaria spp., Trichomosoides spp., Trichinella spp.

From the order of the Rhabditia, for example: Micronema spp., Strongyloides spp

From the order of the Strongylida, for example: Strongylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example: Oxyuris spp., Enterobius spp., Passalurus spp., Syphacia spp., Aspiculuris spp., Heterakis spp.

From the order of the Ascaridia, for example: Ascaris spp., Toxascaris spp., Toxocara spp., Parascaris spp., Anisakis spp., Ascaridia spp.

From the order of the Spirurida, for example: Gnathostoma spp., Physaloptera spp., Thelazia spp., Gongylonema spp., Habronema spp., Parabronema spp., Draschia spp., Dracunculus spp.

From the order of the Filariida, for example: Stephanofilaria spp., Parafilaria spp., Setaria spp., Loa spp., Dirofilaria spp., Litomosoides spp., Brugia spp., Wuchereria spp., Onchocerca spp.

From the order of the Gigantorhynchida, for example: Filicollis spp., Moniliformis spp., Macracanthorhynchus spp., Prosthenorchis spp.

The useful and breeding animals include mammals, such as, for example, cattle, horses, sheep, pigs, goats, camels, water buffaloes, donkeys, rabbits, fallow deer, reindeer, fur-bearing animals, such as, for example, mink, chinchilla or racoon, birds, such as, for example, chickens, geese, turkeys, ducks or ostriches, freshwater fish and sea fish, such as, for example, trout, carp and eels, reptiles and insects, such as, for example, honeybee and silkworm.

The laboratory and experimentation animals include mice, rats, guinea pigs, golden hamsters, dogs and cats.

The hobby animals include dogs and cats.

Administration can be effected prophylactically as well as therapeutically.

The active substances are administered, either directly or in the form of suitable preparations, enterally, parenterally, dermally, nasally, by treating the environment or with the aid of shaped articles containing the active substance, such as, for example, strips, plates, tapes, neck bands, ear tags, limb bands or marking devices.

Enteral administration of the active substances is effected, for example, orally in the form of powders, tablets, capsules, pastes, drinks, granules, solutions which can be applied orally, suspensions and emulsions, boli, medicated feed or drinking water. Dermal application is effected, for example, in the form of dipping, spraying, or pouring-on and spotting-on. Parenteral administration is effected, for example, in the form of injection (intramuscular, subcutaneous, intravenous or intraperitoneal) or by implants.

The following are suitable preparations:
solutions, such as solutions for injection, oral solutions, concentrates for oral administration after dilution, solutions for use on the skin or in body cavities, pour-on formulations, gels;
emulsions and suspension for oral or dermal administration and for injection; semi-solid preparations;
formulations in which the active substance is incorporated in a cream base or in an oil-in-water or water-in-oil emulsion base;
solid preparations, such as powders, premixes or concentrates, granules, pellets, tablets, boli, capsules; aerosols and inhalants, shaped articles containing the active substance.

Solutions for injection are administered intravenously, intramuscularly and subcutaneously.

Solutions for injection are prepared by dissolving the active substance in a suitable solvent and, if desired, adding additives, such as solubilizers, acids, bases, buffer salts, antioxidants, or preservatives. The solutions are sterile-filtered and dispensed into containers.

The following may be mentioned as solvents: physiologically acceptable solvents, such as water, alcohols, such as ethanol, butanol, benzyl alcohol, glycerol, propylene glycol, polyethylene glycols and N-methyl-pyrrolidone, and their mixtures.

If appropriate, the active substances can also be dissolved in physiologically acceptable vegetable or synthetic oils which are suitable for injection.

The following may be mentioned as solubilizers: solvents which facilitate the dissolution of the active substance in the main solvent or which prevent precipitation of the active substance. Examples of solubilizers are polyvinylpyrrolidone, polyoxyethylated castor oil and polyoxyethylated sorbitan esters.

The following are preservatives: benzyl alcohol, trichlorobutanol, p-hydroxy-benzoic esters or n-butanol.

Oral solutions are administered directly. Concentrates are first diluted to the administration concentration and then administered orally. Oral solutions and concentrates are prepared as described above in the case of the solutions for injection, sterile procedures not being necessary.

Solutions for use on the skin are applied drop by drop, smoothed on, rubbed in, splashed on or sprayed on. These solutions are prepared as described above in the case of the solutions for injection.

It may be advantageous to add thickeners in the preparation process. The following are thickeners: inorganic thickeners, such as bentonites, colloidal silica, aluminium monostearate, or organic thickeners, such as cellulose derivatives, polyvinyl alcohols and their copolymers, acrylates and metacrylates.

Gels are applied to the skin or smoothed on or introduced into body cavities. Gels are prepared by adding such an amount of thickener to solutions which have been prepared as described in the case of the solutions for injection that a clear composition is formed which has an ointment-like consistency. The thickeners used are the thickeners indicated further above.

Pour-on and spot-on formulations are poured or splashed onto limited areas of the skin, the active substance penetrating the skin and acting systemically.

Pour-on and spot-on formulations are prepared by dissolving, suspending or emulsifying the active substance in suitable solvents or solvent mixtures which are tolerated by the skin. If appropriate, other auxiliaries, such as colourants, absorption accelerators, antioxidants, light stabilizers or tackifiers, are added.

The following may be mentioned as solvents: water, alkanols, glycols, polyethylene glycols, polypropylene glycols, glycerol, aromatic alcohols, such as benzyl alcohol, phenylethanol or phenoxyethanol, esters, such as ethyl acetate, butyl acetate or benzyl benzoate, ethers, such as alkylene glycol alkyl ethers, such as dipropylene glycol monomethyl ether or diethylene glycol mono-butyl ether, ketones, such as acetone or methyl ethyl ketone, aromatic and/or aliphatic hydrocarbons, vegetable or synthetic oils, DMF, dimethylacetamide, N-methyl-pyrrolidone, or 2,2-dimethyl-4-oxy-methylene-1,3 -dioxolane.

Colourants are all colourants which can be dissolved or suspended and which are approved for use in animals.

Examples of absorption accelerators are DMSO, spreading oils, such as isopropyl myristate, dipropylene glycol pelargonate, silicone oils, fatty acid esters, triglycerides or fatty alcohols.

The following are antioxidants: sulphites or metabisulphites, such as potassium metabisulphite, ascorbic acid, butylhydroxytoluene, butylhydroxyanisole or tocopherol.

Examples of light stabilizers are novantisolic acid.

Tackifiers are, for example, cellulose derivatives, starch derivatives, polyacrylates or natural polymers such as alginates or gelatin.

Emulsions can be administered orally, dermally or as injections.

Emulsions are either the water-in-oil type or the oil-in-water type.

They are prepared by dissolving the active compound either in the hydrophobic or in the hydrophilic phase and by homogenizing this phase with the solvent of the other phase, with the aid of suitable emulsifiers and, if appropriate, other auxiliaries, such as colourants, resorption accelerators, preservatives, antioxidants, light stabilizers, and viscosity-increasing substances.

The following may be mentioned as the hydrophobic phase (oils): paraffin oils, silicone oils, natural vegetable oils, such as sesame seed oil, almond oil or castor oil, synthetic triglycerides, such as caprylic/capric acid biglyceride, a triglyceride mixture with vegetable fatty acids of chain length $C_{8-12}$ or other specifically selected natural fatty acids, mixtures of partial glycerides of saturated or unsaturated fatty acids which may also contain hydroxyl groups, and mono- and diglycerides of the $C_8/C_{10}$-fatty acids.

Fatty acid esters, such as ethyl stearate, di-n-butyryl adipate, hexyl laurate, dipropylene glycol pelargonate, esters of a branched fatty acid having a medium chain length with saturated fatty alcohols of chain length $C_{16}$-$C_{18}$, isopropyl myristate, isopropyl palmitate, caprylic/capric esters of saturated fatty alcohols of chain length $C_{12}$-$C_{18}$, isopropyl stearate, oleyl oleate, decyl oleate, ethyl oleate, ethyl lactate, waxy fatty acid esters, such as artificial duck uropygial fat, dibutyl phthalate, diisopropyl adipate, ester mixtures related to the latter, etc.

Fatty alcohols, such as isotridecyl alcohol, 2-octyldodecanol, cetylstearyl alcohol or oleyl alcohol.

Fatty acids, such as, for example, oleic acid and its mixtures.

The following may be mentioned as the hydrophilic phase: water, alcohols, such as, for example, propylene glycol, glycerol, sorbitol and their mixtures.

The following may be mentioned as emulsifiers: non-ionic surfactants, for example polyoxyethylated castor oil, polyoxyethylated sorbitan monooleate, sorbitan monostearate, glycerol monostearate, polyoxyethyl stearate or alkylphenol polyglycol ethers;

ampholytic surfactants, such as disodium N-lauryl-β-iminodipropionate or lecithin;

anionic surfactants, such as Na lauryl sulphate, fatty alcohol ether sulphates, and the monoethanolamine salt of mono/dialkylpolyglycol ether orthophosphoric ester;

cationic surfactants, such as cetyltrimethylammonium chloride.

The following may be mentioned as other auxiliaries: substances which increase the viscosity and stabilize the emulsion, such as carboxymethylcellulose, methylcellulose and other cellulose and starch derivatives, polyacrylates, alginates, gelatin, gum arabic, polyvinylpyrrolidone, polyvinylalcohol, methylvinyl ether/maleic anhydride copolymers, polyethylene glycols, waxes, colloidal silica, or mixtures of the listed substances.

Suspensions can be administered orally, dermally or as an injection. They are prepared by suspending the active substance in a liquid excipient, if appropriate with the addition of other auxiliaries, such as wetting agents, colourants, resorption accelerators, preservatives, antioxidants and light stabilizers.

Liquid excipients which may be mentioned are all homogeneous solvents and solvent mixtures.

Wetting agents (dispersants) which may be mentioned are the surfactants indicated further above.

Other auxiliaries which may be mentioned are those indicated further above.

Semi-solid preparations can be administered orally or dermally. They are only distinguished from the above-described suspensions and emulsions by their higher viscosity.

To prepare solid preparations, the active substance is mixed with suitable excipients, if appropriate with the addition of auxiliaries, and the mixture is formulated as desired.

Excipients which may be mentioned are all physiologically acceptable solid inert substances. Suitable for this purpose are inorganic and organic substances. Inorganic substances are, for example, common salt, carbonates, such as calcium carbonate, hydrogen carbonates, aluminium oxides, silicas, clays, precipitated or colloidal silicon dioxide, and phosphates.

Organic substances are, for example, sugars, cellulose, foodstuffs and animal feeds, such as powdered milk, animal meals, cereal meals, coarse cereal meals and starches.

Auxiliaries are preservatives, antioxidants and colourants which have already been mentioned further above.

Other suitable auxiliaries are lubricants and glidants, such as, for example, magnesium stearate, stearic acid, talc, bentonites, disintegrants, such as starch or crosslinked polyvinylpyrrolidone, binders, such as, for example, starch, gelatin or linear polyvinylpyrrolidone, and dry binders, such as microcrystalline cellulose.

In the preparations, the active substances can also be present in mixtures with synergists or other active compounds which are active against pathogenic endoparasites. Examples of such active compounds are L-2,3,5,6-tetrahydro-6-phenyl-imidazothiazole, benzimidazole carbamates, pyrantel.

Ready-to-use preparations contain the active substances in concentrations of 10 ppm to 20 per cent by weight, preferably from 0.1 to 10 per cent by weight.

Preparations which are diluted before use contain the active substances in concentrations of 0.5 to 90% by weight, preferably from 5 to 50 per cent by weight.

In the endoparasiticidal compositions according to the invention, where they are employed in the dog as a hobby animal, in general a weight ratio of macrocyclic lactone to depsipeptide of 1:500 to 1000, preferably 1:500 to 850, very particularly preferably 1:500, is observed.

Furthermore, in the endoparasiticidal compositions according to the invention, where they are employed in the cat as a hobby animal, in general a weight ratio of macrocyclic lactone to depsipeptide of 1:150 to 500, preferably 1:150 to 350, very particularly preferably 1:150 to 200, is observed.

Finally, in the endoparasiticidal compositions according to the invention, where they are employed in useful animals, in general a weight ratio of macrocyclic lactone to depsipeptide of 1:20 to 400, preferably 1:20 to 250, very particularly preferably 1:20 to 50, is observed.

In the context of the present invention, the endoparasiticidal compositions can comprise not only at least one macrocyclic lactone and depsipeptides but also praziquantel or epsiprantel. In these cases, the weight ratio of macrocyclic lactone to praziquantel or epsiprantel generally used in the combination according to the invention is that which corresponds to the weight ratio of the depsipeptide.

EXPERIMENTAL SECTION

EXAMPLE A

In vivo nematode test

*Nematospiroides dubius* in the Mouse

Mice are infected experimentally with nematodes of the species *Nematospiroides dubius*. For infection, the mice are administered orally with *Nematospiroides dubius* as 60 filariform larvae.

After the prepatency period has expired, the suspended active substances are administered orally on day 12 after infection.

Determination of the Activity

The mice are selected on day 20 after infection. The adult parasites in the Duodenum are counted by means of a compressor. The success of treatment in the dose group is made relative to the untreated control group.

Tables A and B below indicate the action of the combination against *Nematospiroides dubius* in the mouse.

TABLE A

Action of the combination of PF 1022 A and ivermectin $B_{1a}/B_{1b}$ against *Nematospiroides dubius* in the mouse after oral administration

| Active substance and amount [mg/kg] | | Reduction rate [%] |
|---|---|---|
| PF 1022 A | 50.0 | 0 |
| Ivermectin $B_{1a}/B_{1b}$ | 0.1 | 0 |
| PF1022 A | 50.0 | 100 |
| + Ivermectin $B_{1a}/B_{1b}$ | 0.1 | |
| PF 1022 A | 25.0 | 0 |
| PF1022 A | 25.0 | >80 |
| + Ivermectin $B_{1a}/B_{1b}$ | 0.1 | |

TABLE B

Action of the combination of PF 1022 A and ivermectin $B_{1a}/B_{1b}$ in the presence of praziquantel against *Nematospiroides dubius* in the mouse after oral administration

| Active substance and amount [mg/kg] | | Reduction rate [%] |
|---|---|---|
| PF1022 A | 50.0 | 100 |
| + Ivermectin $B_{1a}/B_{1b}$ | 0.1 | |
| + Praziquantel | 10.0 | |
| PF1022 A | 50.0 | 100 |
| + Ivermectin $B_{1a}/B_{1b}$ | 0.1 | |
| + Praziquantel | 5.0 | |
| PF1022 A | 50.0 | 100 |
| + Ivermectin $B_{1a}/B_{1b}$ | 0.1 | |
| + Praziquantel | 1.0 | |
| PF1022 A | 25.0 | >80 |
| + Ivermectin $B_{1a}/B_{1b}$ | 0.1 | |
| + Praziquantel | 10.0 | |
| PF1022 A | 25.0 | >80 |
| + Ivermectin $B_{1a}/B_{1b}$ | 0.1 | |
| + Praziquantel | 5.0 | |
| PF1022 A | 25.0 | >80 |
| + Ivermectin $B_{1a}/B_{1b}$ | 0.1 | |
| + Praziquantel | 1.0 | |

EXAMPLE B

In vivo nematode test

*Heterakis spumosa* in the Mouse

Mice are infected experimentally with nematodes of the species *Heterakis spumosa*. For infection, the mice are administered orally with *Heterakis spumosa* as 90 embryonate eggs.

After the prepatency period has expired, the suspended active substances are administered orally on day 46 after infection.

Determination of the Activity

The mice are selected on day 54 after infection. The adult parasites are counted in the colon and caecum using a microscope. The success of treatment in the dose group is made relative to the untreated control group.

Tables C and D below indicate the action of the combination against *Heterakis spumosa* in the mouse.

TABLE C

Action of the combination of PF 1022 A and ivermectin $B_{1a}/B_{1b}$ against *Heterakis spumosa* in the mouse after oral administration

| Active substance and amount [mg/kg] | | Reduction rate [%] |
|---|---|---|
| PF 1022 A | 50.0 | 0 |
| Ivermectin $B_{1a}/B_{1b}$ | 0.1 | <50 |
| PF1022 A | 50.0 | 100 |
| + Ivermectin $B_{1a}/B_{1b}$ | 0.1 | |
| PF 1022 A | 25.0 | 0 |
| PF1022 A | 25.0 | 100 |
| + Ivermectin $B_{1a}/B_{1b}$ | 0.1 | |
| PF 1022 A | 10.0 | 0 |
| PF1022 A | 10.0 | >80 |
| + Ivermectin $B_{1a}/B_{1b}$ | 0.1 | |
| PF 1022 A | 5.0 | 0 |
| PF1022 A | 5.0 | >80 |
| + Ivermectin $B_{1a}/B_{1b}$ | 0.1 | |

TABLE D

Action of the combination of PF 1022 A and ivermectin $B_{1a}/B_{1b}$ in the presence of praziquantel against *Heterakis spumosa* in the mouse after oral administration

| Active substance and amount [mg/kg] | | Reduction rate [%] |
|---|---|---|
| PF1022 A | 50.0 | 100 |
| + Ivermectin $B_{1a}/B_{1b}$ | 0.1 | |
| + Praziquantel | 10.0 | |
| PF1022 A | 50.0 | 100 |
| + Ivermectin $B_{1a}/B_{1b}$ | 0.1 | |
| + Praziquantel | 5.0 | |
| PF1022 A | 50.0 | 100 |
| + Ivermectin $B_{1a}/B_{1b}$ | 0.1 | |
| + Praziquantel | 1.0 | |
| PF1022 A | 25.0 | 100 |
| + Ivermectin $B_{1a}/B_{1b}$ | 0.1 | |
| + Praziquantel | 10.0 | |
| PF1022 A | 25.0 | 100 |
| + Ivermectin $B_{1a}/B_{1b}$ | 0.1 | |
| + Praziquantel | 5.0 | |
| PF1022 A | 25.0 | 100 |
| + Ivermectin $B_{1a}/B_{1b}$ | 0.1 | |
| + Praziquantel | 1.0 | |

EXAMPLE C

In-vivo nematode test

*Ancylostoma caninum* in dogs

Beagle puppies were experimentally infested with hookworms (*Ancylostoma caninum*). Amount of infestation material were 250 $L_3$ larvae.

After the prepatent period, when mature worms are present within the gastrointestinal tract, the dogs were orally treated with the test compounds as pure active in gelatine capsules.

Determination of the Efficacy was Carried Out According to the Following Two Methods 1. Counts of worm eggs within the dogs faces before and after treatment.
2. Percent efficacy at a critical test calculated using the formula:

$$\% \text{ efficacy} = \frac{\text{Worms removed}}{\text{Worms removed and worms remaining}} \times 100$$

Table E shows the action of the combination against *Ancylostoma caninum* in dogs.

TABLE E

Action of the combination of PF 1022 A and Ivermectin $B_{1a}/B_{1b}$ against *Ancylostoma caninum* in dogs after oral application

| Active substance and amount [mg/kg] | | Reduction rate [%] |
|---|---|---|
| PF 1022 A | 1,0 | 100 |
|  | 0,5 | 0 |
| Ivermectin $B_{1a}/B_{1b}$ | 0,01 | 100 |
|  | 0,001 | 0 |
| PF 1022 A | 0,5 | >80 |
| + Ivermectin $B_{1a}/B_{1b}$ | 0,001 | |

What is claimed is:

1. Synergistic endoparasiticidal compositions which comprise at least one avermectin, 22,23-dihydroavermectin $B_1$ (ivermectins) or milbemycin from the class of the macrocyclic lactones in combonation with cyclic depsipeptides consisting of amino acids and hydroxycarboxylic acids as ring structural units and 6 to 30 ring atoms, optionally in the presence of praziquantel or epsiprantel.

2. Endoparasiticidal compositions according to claim 1 for dogs, wherein the weight ratio of macrocyclic lactone to depsipeptide is 1:500 to 1000.

3. Endoparasiticidal compositions according to claim 2, wherein said ratio is 1:500 to 850.

4. Endoparasiticidal compositions according to claim 3, wherein said ratio is 1:500.

5. Endoparasiticidal compositions according to claim 1 for cats, wherein the weight ratio of macrocyclic lactone to depsipeptide is 1:150 to 500.

6. Endoparasiticidal compositions according to claim 5, wherein said ratio is 1:150 to 350.

7. Endoparasiticidal compositions according to claim 6, wherein said ratio is 1:150 to 200.

8. Endoparasiticidal compositions according to claim 1 for cattle, horses, sheep, pigs, goats, camels, water buffaloes, donkeys, rabbits, fallow deer, reindeer, mink, chinchilla, raccoon, birds, fish, reptiles and insects, wherein the weight ratio of macrocyclic lactone to depsipeptide is 1:20 to 4000.

9. Endoparasiticidal compositions according to claim 8, wherein said ratio is 1:20 to 250.

10. Endoparasiticidal compositions according to claim 9, wherein said ratio is 1:20 to 50.

11. Endoparasiticidal compositions according to any one of claim 1 characterized in that the ivermectins are selected from the $B_1$ series $B_{1a}$ and $B_{1b}$.

12. Endoparasiticidal compositions according to any one of claim 1 characterized in that the avermectins are selected from the $B_1$ series $B_{1a}$ and $B_{1b}$.

13. Endoparasiticidal compositions according to any one of claim 1 characterized in that the macrocyclic lactones are selected from doramectin and moxidectin.

14. Endoparasiticidal compositions according to any one of claim 1 characterized in that the cyclic depsipeptides are of the formula (III):

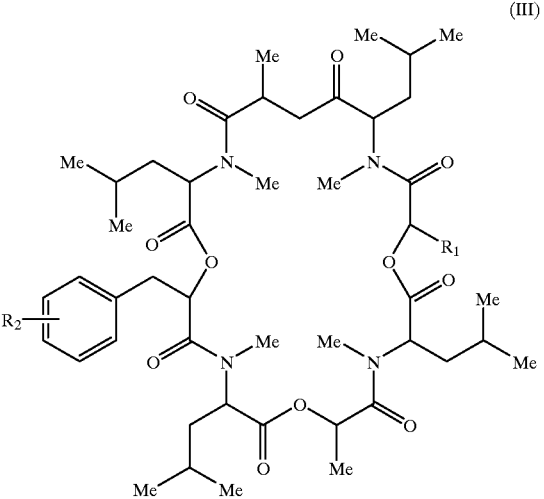

(III)

in which $R_1$ represents benzyl optionally substituted by hydrogen, $C_{1-4}$-alkyl, hydroxyl, halogen, $C_{1-4}$-alkoxy, nitro, amino, dialkylamino, N-morpholinyl, N-pyrrolidinyl or N-piperidinyl, $R_2$ represents hydrogen, $C_{1-4}$-alkyl, hydroxyl, halogen, $C_{1-4}$-alkoxy, nitro, amino, dialkylamino, N-morpholinyl, N-pyrrolidinyl or N-piperidinyl, where
  a) when $R_1$ represents benzyl
    $R_2$ represents hydrogen, hydroxyl, $C_{1-4}$-alkoxy, halogen or alkenyloxy,
  b) when $R_1$ represents methyl
    $R_2$ represents hydrogen, hydroxyl, $C_{1-6}$-alkoxy, nitro, amino, dialkylamino, or N-morpholinyl.

15. Endoparasiticidal compositions according to any one of claim 1 characterized in that the cyclic depsipeptide is of the formula (IIIa):

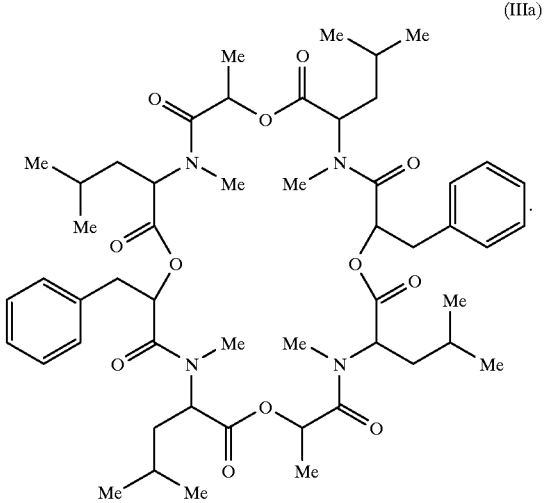

16. Endoparasiticidal compositions according to any one of claim 1 characaterized in that the cyclic depsipeptide is of the formula (IIIb):

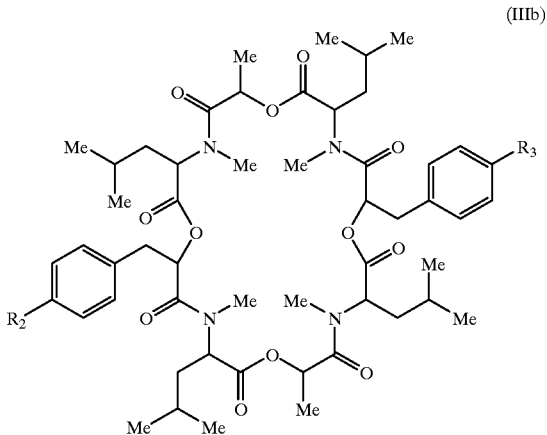

in which $R_2$ and $R_3$ represent N-morpholinyl, nitro, amino, mono- or dimethylamino.

17. Endoparasiticidal compositions according to any one of claim 1 characterized in that the cyclic depsipeptide is of the formula (IIIc):

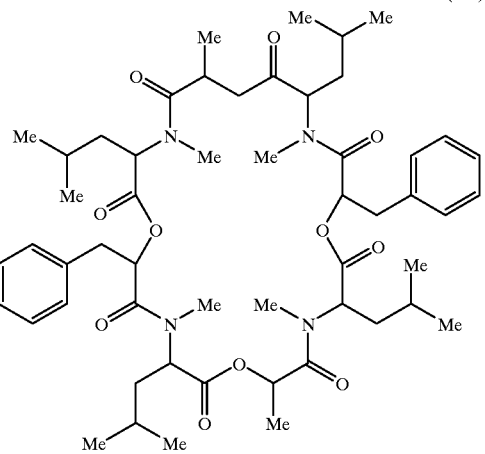

in which $R_2$ represents hydroxyl, methoxy or tert-butoxy.

18. Endoparasiticidal compositions according to any one of claim 1 characterized in that the cyclic depsipeptide is of the formula (IIId):

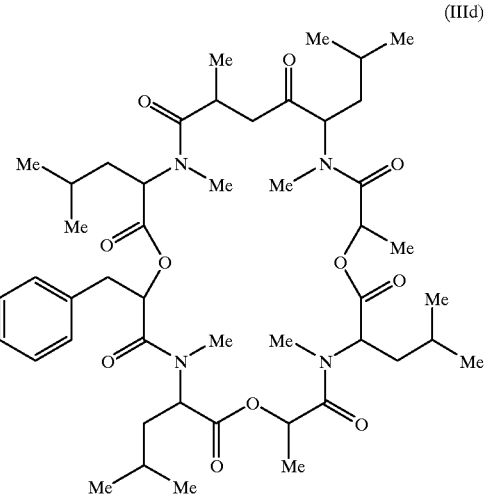

in which $R_2$ represents methoxy, dimethylamino or N-morpholinyl.

19. Endoparasiticidal compositions according to any one of claim 1 comprising a compound of the general formula (Ia):

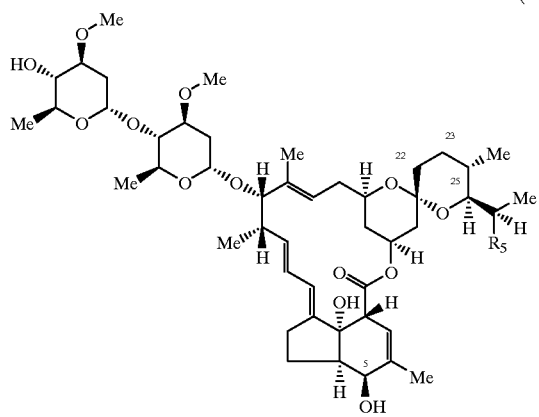

(Ia)

in which

R$_5$ represents methyl and ethyl together with the cyclic depsipeptide PF 1022A of the formula (IIIa)

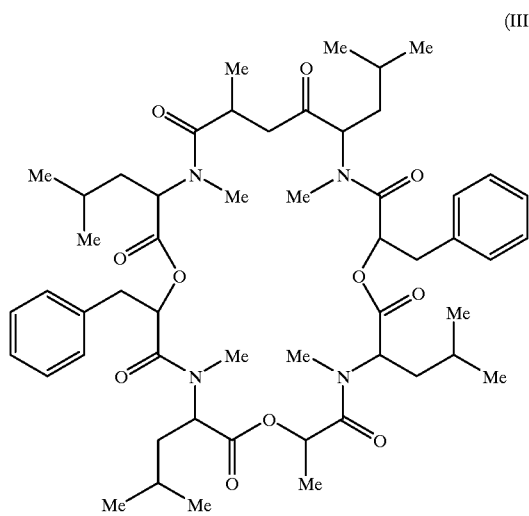

(IIIa)

and optionally praziquantel or epsiprantel.

20. Endoparasiticidal compositions according to any one of claim 1 comprising a compound of the general formula (Ia):

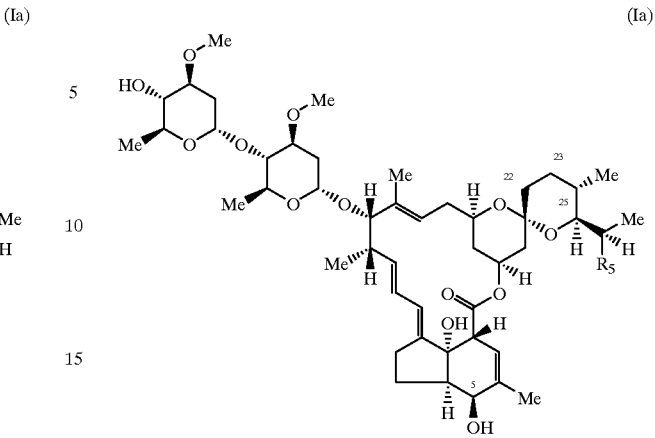

(Ia)

in which

R$_5$ represents methyl and ethyl together with the cyclic depsipeptide of the formula (IIIb)

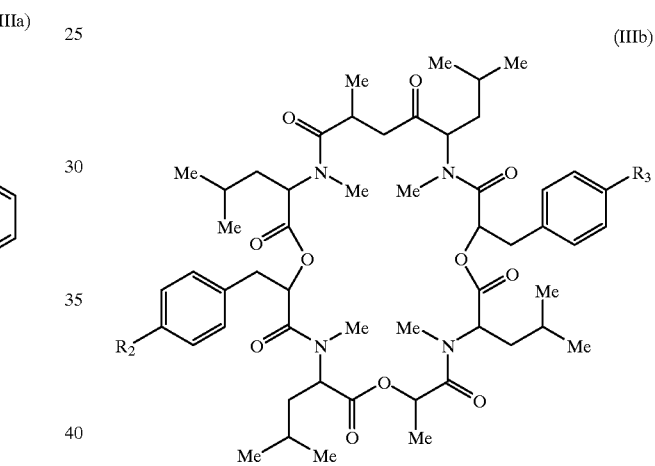

(IIIb)

in which

R$_2$ and R$_3$ represent N-morpholinyl and optionally praziquantel or epsiprantel.

* * * * *